United States Patent [19]

Neukermans et al.

[11] Patent Number: 5,076,692
[45] Date of Patent: Dec. 31, 1991

[54] PARTICLE DETECTION ON A PATTERNED OR BARE WAFER SURFACE

[75] Inventors: Armand P. Neukermans, Palo Alto; Peter C. Jann, Santa Clara; Ralph Wolf, Palo Alto; David Wolze, San Jose; Stanley Stokowski, Danville, all of Calif.

[73] Assignee: Tencor Instruments, Mountain View, Calif.

[21] Appl. No.: 531,132

[22] Filed: May 31, 1990

[51] Int. Cl.⁵ .................... G01N 21/00; G01N 15/06
[52] U.S. Cl. .................... 356/538; 356/237; 356/394; 250/574
[58] Field of Search .................... 356/335-343, 356/237, 356, 394, 398; 250/562, 572, 222.2, 574

[56] References Cited

U.S. PATENT DOCUMENTS

| | | | |
|---|---|---|---|
| 4,180,830 | 12/1979 | Roach | 356/237 |
| 4,188,123 | 2/1980 | Kleinknecht | 356/354 |
| 4,330,213 | 5/1982 | Kleinknecht et al. | 356/355 |
| 4,408,884 | 10/1983 | Kleinknecht et al. | 356/237 |
| 4,598,997 | 7/1986 | Steigmeier et al. | 356/237 |
| 4,731,855 | 3/1988 | Suda et al. | 382/8 |
| 4,740,708 | 4/1988 | Batchelter | 250/563 |
| 4,759,626 | 7/1988 | Korko | 356/124 |
| 4,772,126 | 9/1988 | Allemand et al. | 356/336 |
| 4,806,774 | 2/1989 | Lin et al. | 250/550 |
| 4,812,664 | 3/1989 | Borden | 250/572 |
| 4,898,471 | 2/1990 | Stonestrom et al. | 356/237 |
| 4,952,058 | 8/1990 | Noguchi et al. | 356/237 |
| 4,967,095 | 10/1990 | Berger et al. | 250/572 |

Primary Examiner—Richard A. Rosenberger
Assistant Examiner—Hoa Pham
Attorney, Agent, or Firm—Schneck & McHugh

[57] ABSTRACT

A method and apparatus for predicting the number of contaminant particles in circuit area of a patterned semiconductor wafer having a number of reflective circuit areas. The method includes forming on a wafer in specified areas, a grating test pattern, such as a line grating. The grating patterns are formed at the same time and in the same manner that repetitive circuit patterns are formed on the wafer. The wafer is then scanned by a light beam. Since the diffraction pattern caused by the grating test patterns is known, it is possible to detect when the light beam is scanning one of the known grating patterns. The diffraction pattern may be inspected for fabrication derived variations. In response to detecting a known grating pattern, a detection mechanism is activated. Since the diffraction pattern is known it may be spatially separated. In this way only light scattered by particles or defects in the pattern are collected and detected. From the scattered light that is collected and detected, a particle count may be determined for the grating pattern area. From this particle count an accurate prediction of the number of particles in the circuit patterns may be made. The apparatus may also inspect bare areas. In this manner real time inspection may be performed on patterned wafers.

24 Claims, 5 Drawing Sheets

PARTICLE DETECTION ON A PATTERNED OR BARE WAFER SURFACE

DESCRIPTION

1. Technical Field

The present invention relates to optical surface inspection and more particularly to optical particle detection on patterned semiconductor wafers or the like.

2. Background Art

Detection of particles on patterned semiconductor wafers is becoming a critical step in wafer production. Bare wafers are commonly inspected prior to being processed, and many inspection methods and apparatus have been developed for this purpose. However, it is generally acknowledged that patterned and bare wafers do not collect or indicate particles in the same manner. Therefore, contaminant particle measurements based on bare wafer instruments are often not representative of the real situation on product wafers. Nor are the bare wafer inspection methods of much use on patterned wafers. Thus, other inspection methods and apparatus have been developed for use on patterned wafers.

Bare wafer inspection instruments are generally more sensitive than instruments designed to inspect patterned wafers, usually relying on simple reflectivity or scattering from the wafer.

Patterned wafers, on the other hand, vary greatly in their topography relative to the size of the particles which can disable a circuit on the wafer. The circuit patterns tend to hide particles and make it difficult to distinguish particles from features of the patterns. For this reason, it is difficult to detect particles on the surface of patterned wafers. As a result of this difficulty various methods and apparatus have been proposed for inspecting patterned wafer surfaces and the like.

U.S. Pat. No. 4,740,708 to Batchelder, discloses a method for counting particles on a patterned wafer, by only counting the number of particles on the smooth regions of the wafer. As previously discussed above, it is recognized that smooth and patterned areas do not collect, or generate particles in the same manner or to the same degree.

Methods for detecting defects in the patterned areas of wafers have also been proposed. These methods often involve scanning the patterned areas with a light beam and in some way blocking or filtering out the diffracted light in order to detect defects in the pattern. U.S. Pat. No. 4,731,855 to Suda et al. discloses a method for inspecting pattern defects by scanning the pattern with the light beam normal to the surface and having photodetectors arranged in a plurality of spatial areas which the reflected diffraction patterns do not normally reach. U.S. Pat. No. 4,772,126 to Allemand et al., discloses scanning a patterned wafer at a high angle of incidence and rotating the wafer to minimize the diffracted light. U.S. Pat. No. 4,806,774 to Lin et al., uses a Fourier transform lens and inverse Fourier transform lens to detect defects in wafer patterns. U.S. Pat. No. 4,812,664 to Borden, discloses scanning the wafer surface in an arc at a high angle of incidence and placing a photodetector in close proximity to and directly above the area being scanned.

A common characteristic of the above-discussed methods for detecting particles and defects on patterned areas is that they are inherently slow and often expensive, compared to methods for inspecting bare wafers. Hence, these methods are not suitable for on-line inspection where high speed is of prime concern. These methods also often require complex apparatus. For example, complicated signal processing equipment and techniques are often used to compare and process signals generated by different scans of the same area. In this way, the signals caused by the scattered light from the circuit patterns may be filtered out leaving in theory only the signals caused by particles and defects. However, sharp corners and other such features make this process difficult and lead to inaccurate particle counts. Indeed, it is a difficult and complicated task to design inspection instruments which can efficiently separate the scattered light due to the endless variety of circuit patterns from the scattered light caused by particles.

Non-circuit line and checkerboard patterns have been placed on wafers for various purposes. In U.S. Pat. No. 4,759,626 to Kroko, a line pattern is provided on a wafer for alignment and focusing purposes.

In related U.S. Pat. Nos. 4,188,123 and 4,330,213 to Kleinknecht, diffraction patterns are used to measure a doping concentration or a line width. The diffraction pattern arises from scanning a light beam across actual circuit patterns on a wafer.

In view of the above-described difficulties in detecting particles in patterned wafers, it is an object of the present invention to devise a method and apparatus for determining the number of particles on patterned areas of semiconductor wafers, which method may be accomplished on-line.

It is another object of the present invention to devise inspection apparatus which is simple in design and relatively inexpensive to manufacture.

SUMMARY OF THE INVENTION

The above objects have been achieved by an inspection method and apparatus which is able to detect particles on patterned wafers using a novel test pattern in non-patterned zones of the wafer. The method comprises forming a diffraction grating pattern on a wafer surface in non-circuit areas, such as bare die areas and scribe line zones. The diffraction pattern can be a line grating or other pattern with characteristic beam diffraction directions, and is formed using the same processes as those used to make the circuits on the wafer. Thereafter the wafer surface is scanned by a laser beam in a telecentric manner parallel to itself. Photodetectors are placed at locations where the strong diffraction orders of the diffracted light caused by the diffraction grating pattern will occur. In this way, periods when the beam is scanning a diffraction grating pattern, as opposed to a circuit area, will be identified, and data gathered by collection and detection means will be analyzed in response to the grating pattern being identified. For purposes of particle detection, the scattered light from non-grating areas is spatially separated from the diffracted light from gratings, so that only the scattered light caused by particles or defects in the grating areas reach the collection means. The collected light is then detected by another photodetector so that an accurate count of the number of particles within the grating pattern areas may be determined. From this count an extrapolated projection of the number of particles in the circuit areas may be determined based on the area of the gratings compared to the circuit areas. Bare areas may also be provided which can either be identified in a first pre-scan of the wafer at low photodetector gain and inspected in a second data scan at higher gain, or, alternatively, be identified and inspected in a single scan with the aid of an automatic gain switching circuit. These bare areas provide an estimate of wafer contamination prior to patterning, for comparison with contamination after patterning.

The apparatus includes a laser beam source and optics which produce a beam having a diameter which is large enough to cause diffraction from the grating, for example by spanning across several periods of a line and space grating pattern. The laser beam is caused to scan over the wafer, preferably in a telecentric manner. The apparatus further includes a wafer holding means and means for moving the wafer in a direction perpendicular to the scan line so that the entire wafer can be scanned.

Because the size and location of the diffraction grating pattern on the wafer is known, it can be identified by monitoring the presence of the strong diffraction orders of the diffracted light at designated places in the Fourier plane. Thus, the instrument also includes photodetectors which are located at those designated places for indicating when the beam is in a grating pattern area. For particle detection, the collection system is advantageously designed to not collect specularly reflected light or the diffracted light, but only the scattered light. The collection means may take the form of an elliptical cylinder mirror serving as a first collector having a slit therein for admitting the laser beam. The specularly and diffracted light also leaves the first collector system through a slit. A collection lens directs diffracted light to diffraction detectors regardless of the position of the beam on the scan line. A fiberoptic bundle coupled to a photodetector serves as a second collector in the collection means and may be placed at one focus of the elliptical mirror while the beam scan line is at the other focus so that the scattered light collected by the mirror may be measured. The particle detection photodetector may be active only when the beam is in grating pattern areas, and may be activated by a signal derived from the pattern identification photodetectors. Spatial and temporal filtering can be applied to further reduce the effects of stray light scattered by the grating. For example, the collection means may be positioned to enhance collection of particle scattered light relative to pattern scattered light, and thereby reject most pattern scattered light.

An advantage of the present invention is that the light gathering systems can be designed to physically exclude the scattering caused by the diffraction grating pattern since its light scattering pattern is known. As a result, it is possible to significantly increase the sensitivity of the instrument, because the light gathering properties of the collection system can be appreciably enhanced. Moreover, the special nature of those patterns allows for their automatic detection, which greatly reduces the complexity of the instrument, since the instrument is designed for a known diffraction pattern rather than an endless variety of patterns.

The present invention also gives an accurate prediction of the number of particles in the patterned circuit areas of a wafer, since the same processes which are used to form the circuit patterns are also used to form the diffraction grating pattern. Since only the particles in the known diffraction grating pattern areas need to be counted, a wafer can be inspected very quickly. This is important for on-line inspection.

BEST MODE FOR CARRYING OUT THE INVENTION

Figure 1:
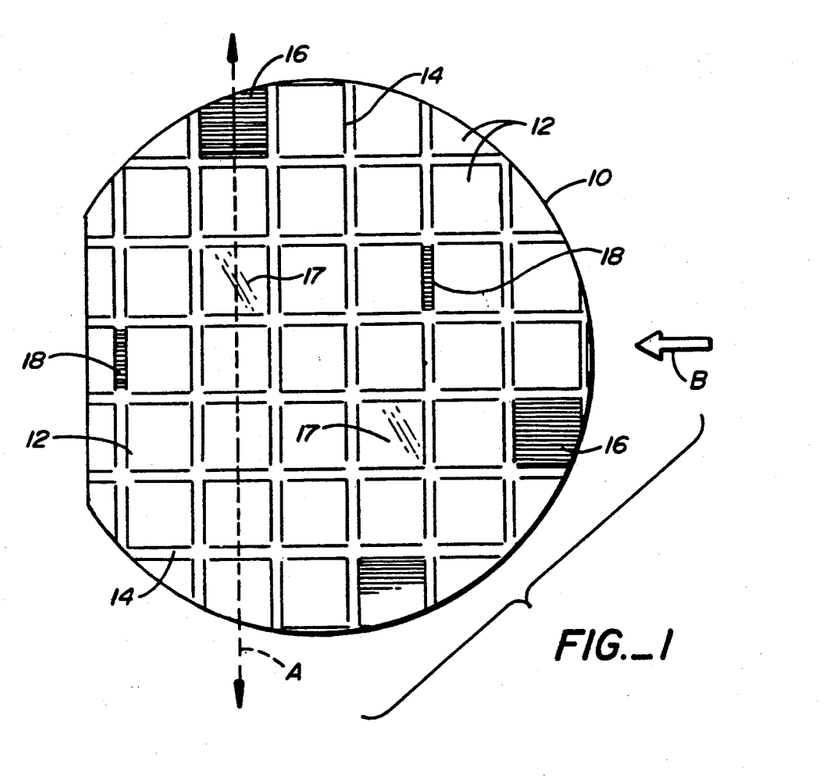
FIG. 1 is a plan view of a patterned semiconductor wafer in accord with the present invention.

Referring to FIG. 1, a patterned wafer 10 is shown having die areas 12 delimited by streets 14. The wafer 10 contains diffraction grating patterns 16 and 18 in selected sites. The grating patterns 16 are located in die areas, while the grating patterns 18 are located in streets. Either or both grating patterns may be used on a wafer. Most commonly, a grating pattern will be a series of very thin parallel lines, with a period of a few microns, assuming illumination by light having a wavelength of 400–700 nm. The die areas used to contain grating patterns 16 typically are areas which are commonly not used to create circuit patterns. In this way there would be no loss in the number of circuits produced on the wafer. Die areas 17 which contain neither circuit patterns nor grating patterns, but are instead bare may also be included for comparison with grating pattern areas 16. Likewise, some streets may also be bare.

The diffraction grating patterns 16 and 18, are typically made up of lines and spaces. The periodicity of these lines and spaces is chosen such as to be different, if possible, from any circuit pattern. The grating patterns are orientated to coincide with the wafer streets 14, that is either perpendicular or parallel to the streets. Grating patterns other than lines and spaces that have characteristic diffraction patterns which can be collected in directions distinct from scattered light may also be used.

Figures 2, 3:
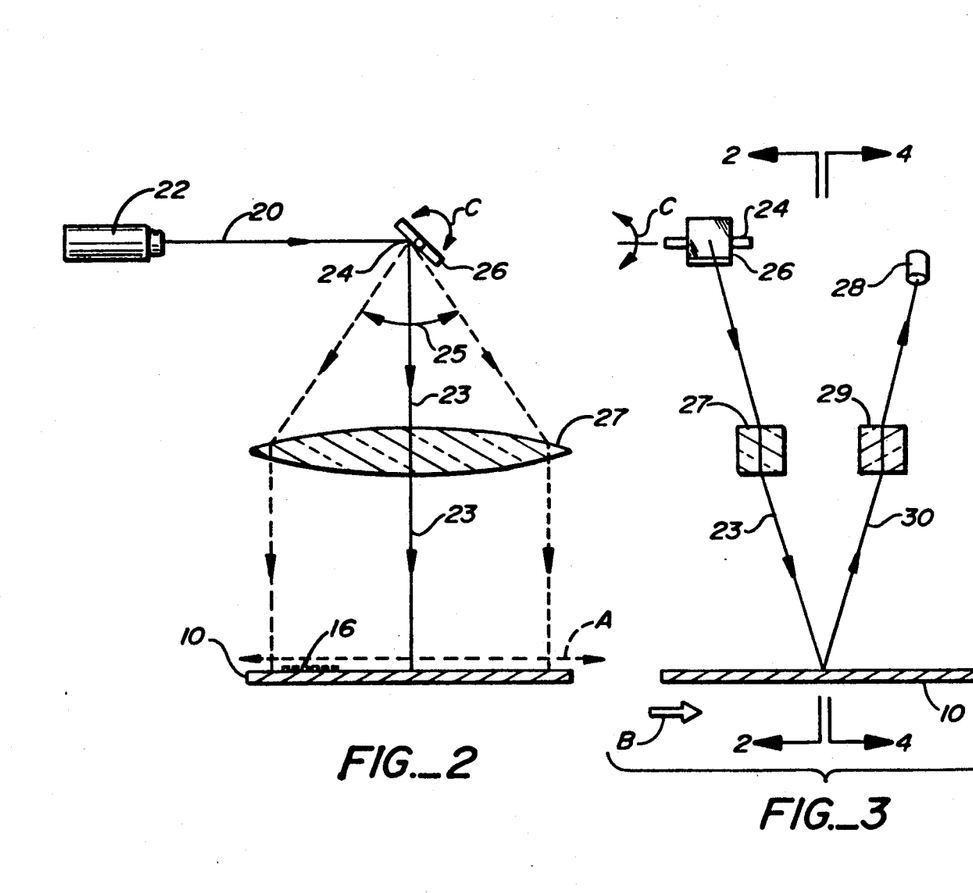
FIGS. 2–4 are partial front, side and rear views of an embodiment of the present invention.
Figure 4:
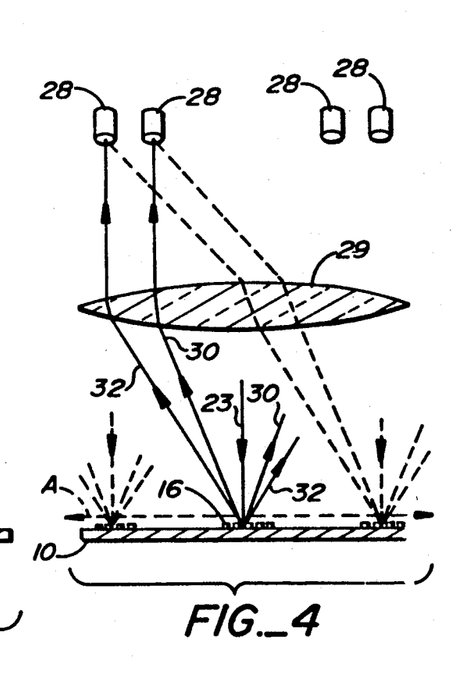

Turning now to FIGS. 2–4, wafer 10 is shown while being scanned. A laser beam source 22 directs a laser beam 20 to a mirror 26 which pivots on a spindle 24 in a direction indicated by arrow C. The mirror 26 directs the laser beam 20 toward the surface of wafer 10 in a scanning motion 25. The scanning beam 23 passes through a lens 27 having a focal point at the point where the beam 23 leaves the mirror 26. For an $f-\phi$ lens, the beam 23 scans the wafer 10 in a telecentric manner, i.e. parallel to itself. Other telecentric scanners may also be used.

A laser beam 23 scans over the wafer 10, such that the illumination, path aligns itself with the wafer streets 14 which may be seen in FIG. 1. Prior to being scanned, the wafer 10 is aligned so that the streets 14 are aligned with the scan. Dashed line A in FIGS. 1, 2 and 4 represents the scan line.

The wafer 10 is moved mechanically in a perpendicular direction, indicated by arrow B in FIGS. 1 and 3, relative to scan line A. Laser beam 23 preferably has a diameter as small as possible, for detection purposes, but must be large enough to contain several periods of the line and space pattern of the grating. This enables pronounced diffraction to take place when the laser beam 23 lands on the grating patterns 16 and 18. Presently, beam diameters within the range of 20–40 μm are preferred. However, larger or smaller beam sizes may be desirable dependent upon the dimensions of the features involved on the wafer surface and the critical size of the particles.

When the laser beam 23 starts scanning over the wafer 10, scattering takes place in a variety of possible directions. The presence of grating patterns 16 and 18 is detected by monitoring the presence of the strong diffraction orders at designated places in the Fourier plane. This is possible because the period of the pattern is known. In order to detect grating pattern locations, photodetectors 28, shown in FIGS. 3 and 4, are provided. When the beam reaches one of the grating patterns 16 or 18, the light is diffracted in a known pattern. Light beam 30 represents the first order of this diffraction pattern, and light beam 32 represents the second order of the diffraction pattern. The photodetectors 28 are situated with respect to laser beam 23 such that the first and second orders of the diffraction pattern are detected. Alternatively, a detector array may be used in place of individual detectors 28 so as to monitor deviations from expected or target diffraction pattern locations. By this means one can measure the grating line width, the line-to-space width ratio, the smoothness or roughness of the grating and other process dependent variations of the grating patterns, thereby providing an incidental prediction of integrated circuit pattern quality.

In order that the diffracted light 30 and 32 will reach detectors 28 regardless of the position of the scanning beam 23 in the scan path A, and thus of the origin on the wafer 10 of the diffracted light 30 and 32, a lens 29 may be placed in the diffracted light path between the wafer 10 and the detectors 28. The wafer 10 lies in the first focal surface of lens 29, while detectors 28 lie in the second focal surface of lens 29 at characteristic diffraction order locations. Lens 29 should be sufficiently wide to accept at least first order diffracted light and preferably also second order diffracted light from all scan positions on wafer 10.

Figure 5:
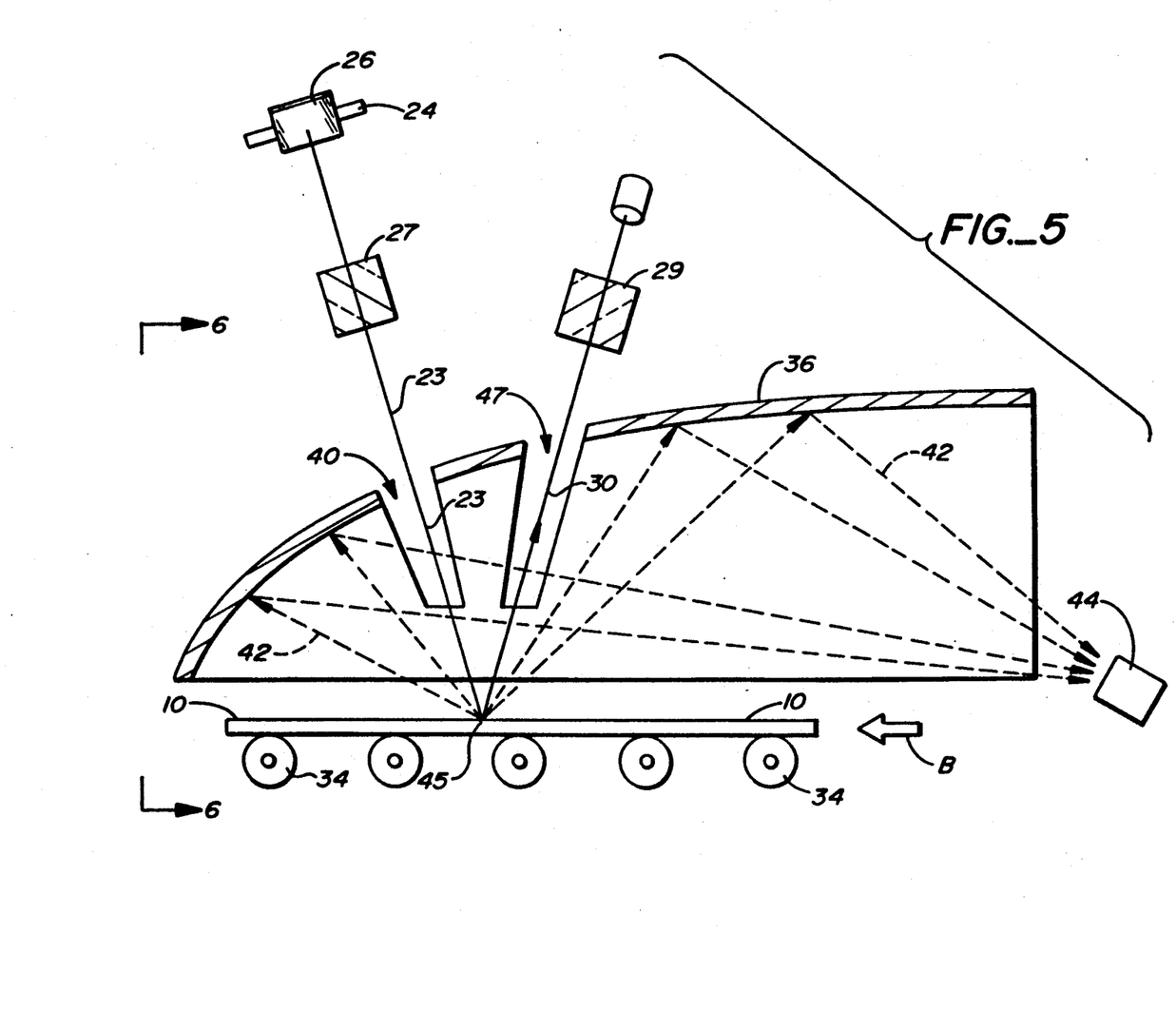
FIG. 5 is a detailed side view of the embodiment shown in FIGS. 2–4.

In any case, a signal is derived that unambiguously indicates when the scanning beam 23 has reached the grating areas to be inspected. When beam 23 scans these areas 16 or 18, particle scattering information gathered by a collection and detection means, like that shown in FIG. 5, is retained for analysis. Information is generally ignored when the beam 23 leaves grating areas 16 and 18 until the beam reaches the next area 16 or 18 to be inspected. For example, a light detector 44 of the collection and detection means may be gated on and off by external control signals generated from diffraction order detectors 28, described above, or from a pre-scan identifying bare areas, as described below. Alternatively, light detection may be gated on and off by a control circuit that is internal to the detection system, such as that described below for FIG. 8. Light detection may even be continuous, in which case selection of data to be analyzed may occur subsequent to detection.

Because the grating pattern is well known in, advance, it is therefore possible to predict in which direction light from it will normally diffract. For example, for any line grating pattern very little diffraction should take place in a line perpendicular to the plane of the grating lines. On the other hand, locations for diffraction patterns may be observed and recorded for particular gratings. It is therefore possible to provide collection systems which reject known patterns of diffracted light, yet which are very effective in collecting light scattered differently by a particle. Spatial filtering can be applied to reduce the light scattered by the grating. This principle can be extended to grating patterns other than line patterns.

Figure 6:
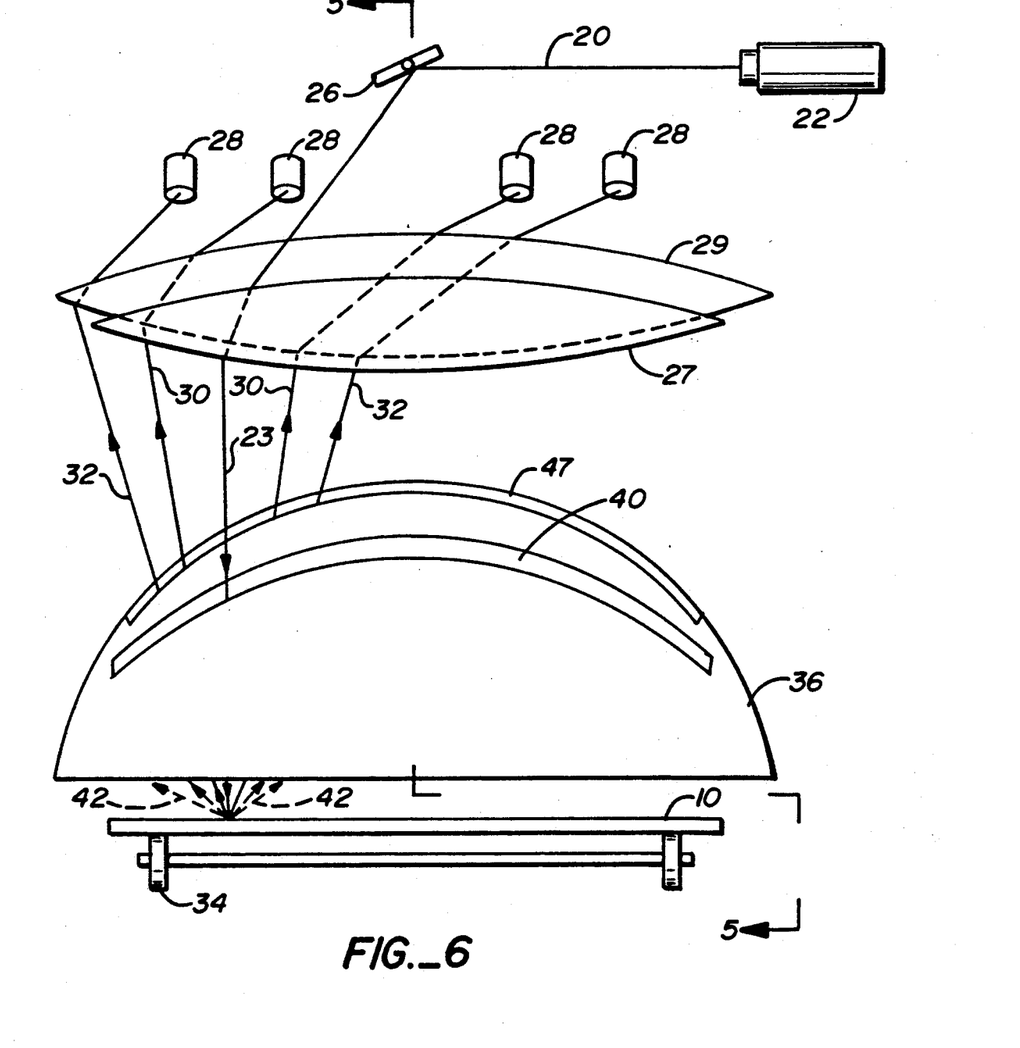
FIG. 6 is a front view taken along the lines 5—5 of FIG. 5.

FIGS. 5 and 6 illustrate one such embodiment of a collection and detection means. The apparatus includes a wafer transport means 34, which may be accomplished by any of the known wafer transport devices. The collection and detection means itself comprises a light collector 36 having an elliptically shaped reflective surface which has a first slit 40 defined therein. The slit 40 allows admittance of the scanning laser beam 23 so that when the wafer 10 is positioned beneath the light collector 36 the laser beam 23 may be scanned along a line across the surface of the wafer. As the beam 23 scans across the wafer surface, it will come across the grating patterns 16 and 18. These produce the diffracted light beams 30, which exit through a second slit 47. This is so, since the diffraction orders are directed along a line parallel to the scan line when the line gratings are perpendicular to the scan line. Therefore a slit 47 may be designed so that nearly all of the diffracted light leaves the enclosure. However, light rays 42, which are scattered rays caused by particles, strike the surface of the light collector 36 and are directed onto photodetector 44. Collector 36 is an elliptical cylinder in cross section, with a scan line 45 at one focal line of the elliptical cylinder and photodetector 44 at the other focal line. The photodetector 44 generates an electrical signal in response to scattered light reaching it, and particles may be indicated whenever the electrical signal exceeds a predetermined threshold. In this way particles in the grating patterns 16 and 18 may be detected and counted. As already noted above, photodetector 44 is only active when the beam is scanning grating areas 16 or 18.

Since the grating patterns are made using the same processes used to make circuit patterns, a close approximation of the number of contaminant particles in the circuit unit areas may be made from the particle counts in unit areas of the grating patterns. Overall wafer particle counts are extrapolated from the particle counts in the grating areas 16 and 18. Inspection of patterned wafers in the above-described manner may be done on-line during the manufacturing process. Indeed, the grating patterns and circuit patterns may be formed at the same time. This would result in immediate detection of a production problem before the circuits are implemented or tested. This also allows for the isolation of the problem source.

Considering FIGS. 1 and 5 wafer inspection may also occur in a two-scan process. In a first pre-scan, grating areas 16 and 18 are detected and inspected as described above. Photodetector 44 is always active but at low gain in nongrating areas. Nongrating areas are not inspected for particles, but the amount of scattering is observed to identify bare streets and bare die areas 17 on the wafer 10. Low detector gain is necessary to prevent saturation of the photomultiplier tube or other detector 44 when circuit pattern areas are being scanned. Locations of bare areas 17 are stored in a memory. In a second data scan, photodetector 44 is at low gain except in identified bare areas 17 where the detector gain is increased. Bare areas can then be inspected for particles with high sensitivity. The results can then be compared with detection counts and particle size distributions in grating pattern areas 16 and 18.

Figure 8:
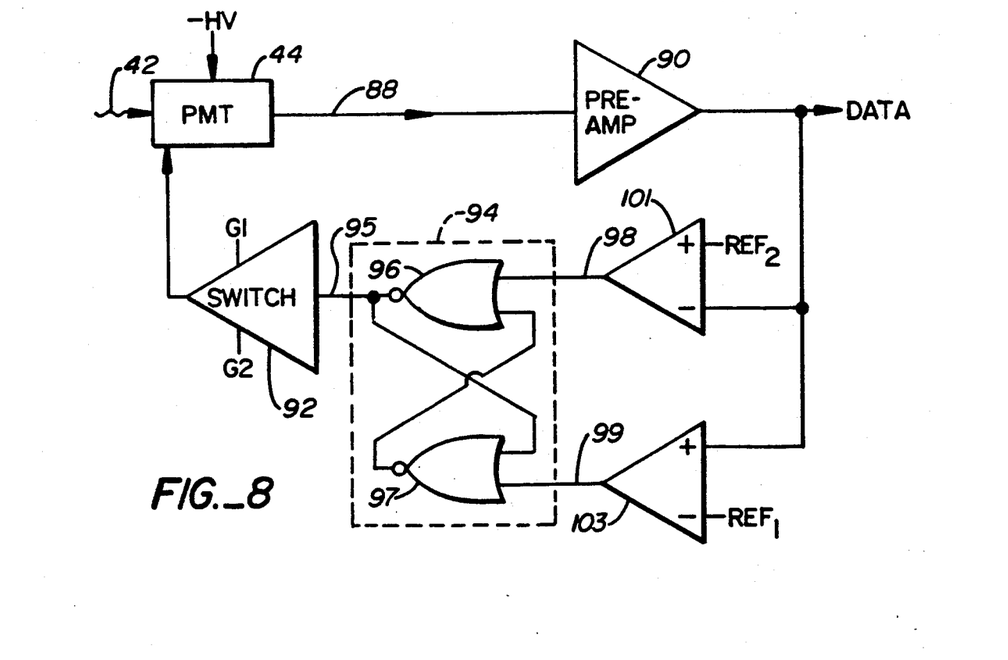
FIG. 8 is a schematic circuit diagram of a gain control circuit for a photodetector used with the present invention.

Alternatively, the bare wafer areas 17 may be identified and inspected in a single scan, eliminating the first pre-scan and consequently eliminating the need to assure exact retracing on the subsequent data scan, by deciding during a scan itself whether the photomultiplier tube (PMT) 44 should be disabled or re-enabled. Referring to FIG. 8 this may be done by monitoring the electrical output 88 of the PMT 44, and switching the PMT 44 between a high or low gain state depending on the amplitude of the output signal 88. The embodiment makes use of a two-state (binary) automatic gain switching circuit for providing these monitoring and switching functions. The PMT 44 and a pre-amp 90 produce a signal DATA that is proportional to the brightness of the incoming light signal 42. The proportionality constant or "gain" is set to one of two values, high gain G1 or low gain G2, by a fast, high voltage switching circuit 92. The ratio of the two gains G1/G2 will be about 1000. This fast switching circuit 92 is controlled by an S-R type flip-flop 94, represented here by a pair of cross-coupled NOR gates 96 and 97, with an output 95 connected to a control input of switching circuit 92. The flip-flop 94 also has a pair of inputs 98 and 99 connected to outputs of respective comparators 101 and 103. Each comparator receives, as one input, the data signal DATA from pre-amp 90. Each comparator 101 and 103 also receives, as the other input, a reference signal $REF_2$ or $REF_1$. The S-R flip-flop 94 is forced by comparators 101 and 103 to change state under one of two conditions. If the PMT 44 is running at high gain G1 and the output signal DATA exceeds the threshold set by $REF_1$, the PMT is forced into the low gain mode. If the PMT 44 is running at low gain G2 and the signal DATA drops below the threshold set by $REF_2$, the PMT is forced into the high gain mode. In this way, the PMT 44 automatically switches to low gain G2 when the light signal exceeds a safe operating level for the PMT, and resets itself to high gain G1 when the light signal returns to a level where it is safe to do so, i.e. when bare areas on a wafer are being scanned.

The suggested techniques and apparatus make use of the fact that the geometries of the grating patterns are known, and therefore the light gathering systems may be designed to exclude the scattering of these patterns. As a result, the sensitivity of the system may be significantly increased, because the light gathering properties of the collection system can be appreciably enhanced. Moreover, the special nature of those patterns allows for their automatic detection, which greatly reduces the complexity of the instrument.

Other collection schemes from that shown in FIGS. 5 and 6 are possible. For example, it is possible to construct a scattered light collection system that spatially filters out unwanted scattering due to the pattern. Used in conjunction with this invention, this would reduce the collection of any stray light scattered by the grating. Thus, in FIG. 7, such an apparatus is shown. It has a light source 50, such as a laser, emitting a beam 52 that passes through a polarizing filter 54. Alternatively, a laser light source 50 may produce a polarized laser beam. In either case, the resulting polarized beam 56 has a polarization which is substantially parallel to the surface of a wafer 66. Beam 56 may pass through a beam expander 58 to attain a diameter as large as 100 μm, but typically about 20–40 μm. A deflection mirror 60 pivots on a spindle 61 as indicated by arrows D, causing the beam 64 to scan over wafer 66 in a direction shown by the solid line beam 64 in comparison to the dashed line beam 64. A lens 62 with a focus at mirror 60 causes the beam to scan telecentrically. Beam 64 is incident at a shallow angle $\theta_i$, typically about 5 to 20 degrees with respect to the wafer surface.

Figure 7:
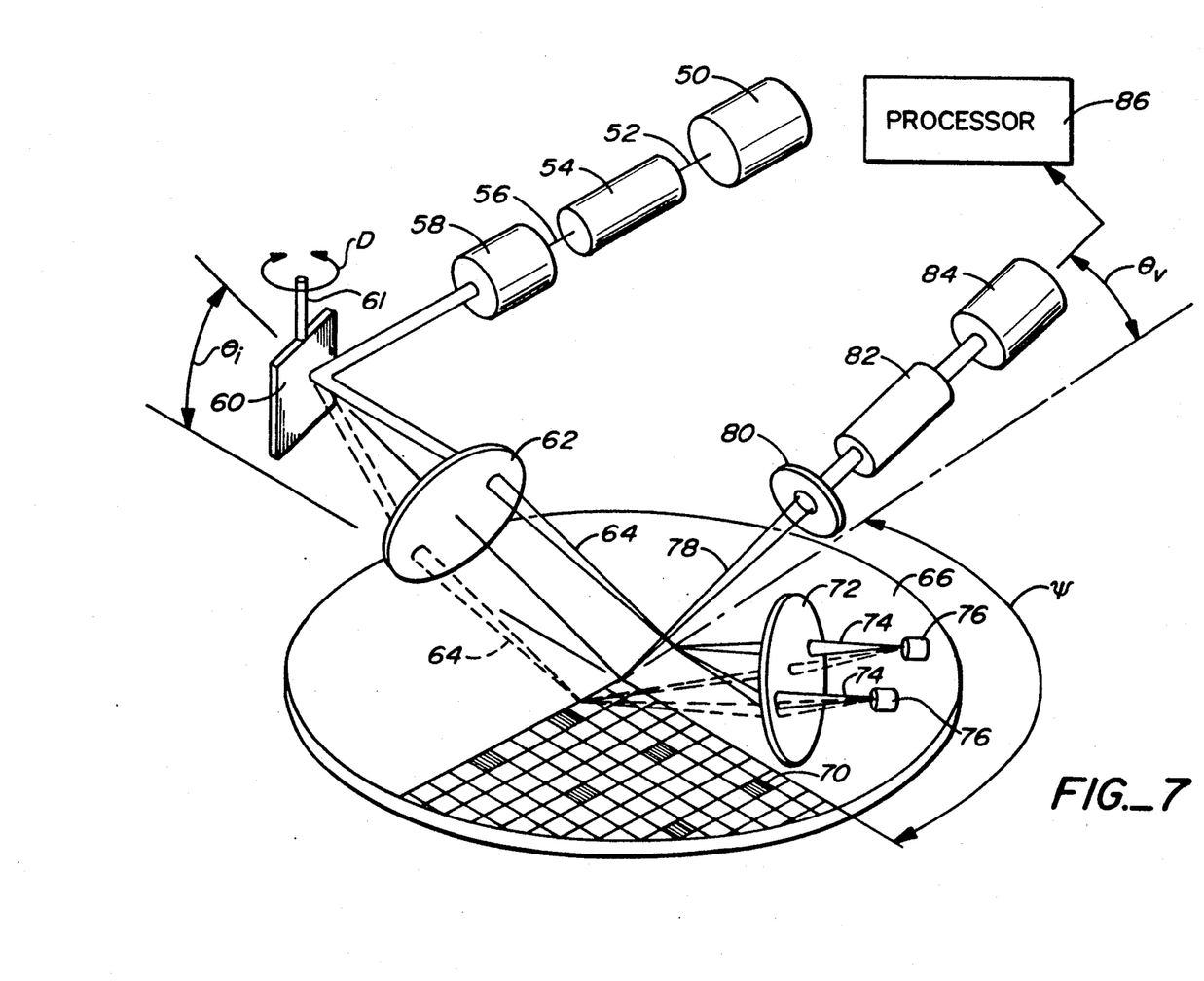
FIG. 7 is a perspective view of an alternate embodiment in accord with the present invention.

As in the previous embodiments, wafer 66 has die separated by a grid of streets indicated by the intersecting lines on wafer 66 and the wafer 66 is aligned prior to scanning so that the scan path is aligned parallel to one direction of the streets 68. 30 Wafer 66 also has grating patterns 70 located in unused die areas and in wafer streets which may be line and space patterns oriented perpendicular to the scan direction. Light 74 diffracted by the grating patterns 70 are directed by a lens 72, used in a telecentric fashion, to a set of detectors 76 positioned for receiving at least the first order and preferably additional orders of diffracted light. Lens 72 images the scan-line onto the detectors 76 so that the diffracted light will be received at the same locations regardless of the position of the beam 64 in the scan. The diffraction detection optics are oriented at a shallow angle above the wafer surface that should be substantially equal to the incidence angle $\theta_i$ for a line type grating pattern. The optic axis of lens 72 is positioned at an azimuthal angle of 0° relative to the incident beam direction, while the detectors 76 are positioned at expected diffraction locations.

Light 78 scattered by particles and other surface flaws from wafer 66 is collected by a collection system that includes collimating and focusing optics 80, a polarizing filter 82 that polarizes the collected light parallel to the wafer surface and a detector 84, such as a photomultiplier tube. Detector 84 produces an electrical signal corresponding to the intensity of scattered light collected by the collection system, which signal is directed to a processor 86 for analysis. The position of the light collection system is such as to receive a minimum of light scattered by the pattern and thereby maximize the ratio of particle signal to pattern signal. Accordingly, the collection system is oriented to receive light 78 at an elevation angle $\theta_v$ which is less than 15 degrees above the wafer surface and at an azimuthal angle relative to the incident beam direction in a range from about 80 to 100 degrees. Preferably light collection is uniform with an approximately constant (within about 15%) solid angle of acceptance by optics 80 for all points on the wafer. When the laser beam is scanned with a constant beam velocity, the stray light of the grating which reaches the photodetector will give rise to a periodic signal. Hence, temporal filtering of the signal can further reduce the effect of the stray light caused by the grating.

A variant of these approaches is to make the grating period small enough so that the diffracted orders are beyond 90 degrees, which is physically impossible. The incident and scattered light are connected by the equation:

$$\sin \theta_s = \sin \theta_i + n \frac{\lambda}{d}$$

where n=0 corresponds to undiffracted light, n=1 the first order, etc. The grating period is d and λ the wavelength of light. Here $\theta_i$ and $\theta_s$ are the incidence and scattering angles with respect to the normal to a surface for a line type grating pattern. For $\theta_i=0°$, $\theta_s=90°$ at λ=d. For shorter grating periods, the scattered light goes into surface modes with the region appearing to have low reflectivity. One need, therefore, no longer worry about the diffracted beams, and therefore, the gratings will appear as bare areas of low reflectivity. Hence, under those conditions, all of the above schemes which apply to bare wafer areas also apply to these gratings.

We claim:

1. A method of estimating the number of particles on patterned areas of a wafer surface, comprising the steps of:
   providing on a wafer surface having circuit pattern areas thereon, a diffraction grating pattern in at least one area other than said circuit pattern areas, said diffraction grating pattern having a characteristic diffraction which is distinguishable from light scattering from said circuit pattern areas;
   scanning the surface with a light beam;
   separating diffracted light due to the diffraction grating pattern from scattered light;
   collecting and detecting the scattered light;
   analyzing a data signal derived from detecting said scattered light whenever said light beam is in an area containing said diffraction grating pattern;
   establishing a particle count for the area containing the diffraction grating pattern from the detection of the scattered light; and
   extrapolating the number of particles on circuit pattern areas from the established particle count for diffraction grating pattern areas.

2. The method of claim 1 further comprising the step of providing a plurality of diffraction grating patterns on said surface.

3. The method of claim 2 wherein said diffraction grating pattern is a series of parallel lines having a width of less than 2 microns.

4. The method of claim 3 wherein said diffraction grating pattern is provided in a street on said wafer.

5. The method of claim 1 wherein said light beam scans said surface telecentrically.

6. The method of claim 1 wherein said step of providing a diffraction grating pattern takes place at the same time as making circuit patterns on said surface.

7. The method of claim 1 wherein said scattered light is detected at low gain when said light beam is in areas other than those containing diffraction grating patterns, at least some areas of said surface being bare, locations of said bare areas being identified by said low gain detection and stored in a memory, the method further comprising repeating the scanning of said wafer and the collecting and detecting of scattered light, the detecting of scattered light being at a high gain when said light beam during said repeated scan is in an identified and stored bare area location, whereby a comparison particle count is established for said bare areas.

8. The method of claim 1 wherein said scattered light is detected with a selected one of two gain levels, the gain level being switched from a high gain level to a low gain level whenever a detected light signal exceeds a first reference value, the gain level being switched form the low gain level to the high gain level whenever the detected light signal falls below a second reference value.

9. A method of estimating the number of particles on circuit patterned areas of a semiconductor wafer during manufacturing processes, the method comprising the steps of:
   providing a wafer to a wafer processing system;
   forming a grating test pattern in at least one grating area on a surface of the wafer using the processes of the wafer processing system, the grating test pattern having a characteristic diffraction unique from that of circuit patterns on the wafer;
   providing the wafer to a surface inspection system;
   scanning the surface of the wafer bearing the grating pattern with a light beam;
   separating diffracted light due to said grating test pattern from scattered light;
   collecting and detecting the scattered light of the first grating test pattern;
   analyzing a data signal derived from detecting said scattered light, said analyzing occurring only when said light beam is scanning said grating area, thereby establishing a particle count for the grating test pattern; and
   extrapolating the number of particles on circuit patterned areas of the wafer based from the particle count for the grating test pattern.

10. The method of claim 9 wherein said wafer is provided with a plurality of grating test patterns, each having the same characteristic diffraction as said grating test pattern.

11. The method of claim 10 wherein said plurality of grating test patterns are disposed in streets or die areas of said wafer.

12. The method of claim 9 wherein said grating test pattern is formed concurrently with circuit patterns on said wafer.

13. The method of claim 9 further comprising the step of identifying said grating test pattern by detection of said characteristic diffraction.

14. The method of claim 13 wherein said analyzing step is activated in response to said identifying of said grating test pattern.

15. The method of claim 13 wherein said identifying of said grating test pattern further includes analyzing said detected diffraction for deviations from an expected diffraction, whereby any wafer processing derived variations in forming said grating test pattern are identified.

16. A surface inspection instrument for a surface having periodic patterns and grating test patterns amid the periodic patterns comprising:
    a light beam source;
    means for holding a surface in scanning relation to the light beam source;
    means for scanning the light beam across the surface;
    means for recognizing a characteristic diffraction from a grating test pattern on the surface;
    means for separating the diffracted light caused by the grating test pattern from light scattered from the surface;
    means for collecting the scattered light; and
    means for detecting the collected light.

17. The instrument of claim 16 wherein said light beam source is a laser.

18. The instrument of claim 16 wherein said means for recognizing said characteristic diffraction includes photodetectors located at predetermined sites relative to said light beam, the sites including the first and second diffraction orders of the diffracted light caused by the grating pattern.

19. The instrument of claim 16 further comprising means for analyzing a data signal derived from said means for detecting the collected light.

20. The instrument of claim 16 wherein said means for collecting comprises a cylindrical elliptical mirror, said means for separating the diffracted light comprising an opening in said mirror at characteristic diffraction locations.

21. The instrument of claim 20 wherein said means for collecting further comprises an optical bundle at a focus of said elliptical mirror.

22. The instrument of claim 16 wherein said means for holding is associated with a means for providing relative planar motion to the surface.

23. The instrument of claim 16 wherein said light beam is polarized parallel to said surface and incident on said surface at a shallow elevational angle, said means for collecting comprising collecting and collimating optics and a polarizer positioned to accept scattered light at a shallow elevational angle and an azimuthal angle in a range from about 80 to about 100 degrees relative to said incident light beam and with a polarization parallel to said surface, said accepted light being directed to said means for detecting.

24. The instrument of claim 16 further comprising:
means responsive to a data signal derived from said detecting means for comparing said data signal with a pair of reference signal levels; and
means responsive to said comparing means for rapidly switching a gain of said detecting means between a pair of gain levels, said gain level being switched from a high gain to a low gain whenever said data signal exceeds a first reference signal level, said gain level being switched from a low gain to a high gain whenever said data signal falls below a second reference signal level.

* * * * *